United States Patent
Zhang et al.

(10) Patent No.: US 11,227,403 B2
(45) Date of Patent: Jan. 18, 2022

(54) ANISOTROPIC TWICING FOR SINGLE PARTICLE RECONSTRUCTION USING AUTOCORRELATION ANALYSIS

(71) Applicant: The Trustees of Princeton University, Princeton, NJ (US)

(72) Inventors: Teng Zhang, Oviedo, FL (US); Amit Singer, New York, NY (US); Tejal Bhamre, Mountain View, CA (US)

(73) Assignee: The Trustees of Princeton University, Princeton, NJ (US)

( * ) Notice: Subject to any disclaimer, the term of this patent is extended or adjusted under 35 U.S.C. 154(b) by 205 days.

(21) Appl. No.: 16/605,987

(22) PCT Filed: Apr. 24, 2018

(86) PCT No.: PCT/US2018/029152
§ 371 (c)(1),
(2) Date: Oct. 17, 2019

(87) PCT Pub. No.: WO2019/018040
PCT Pub. Date: Jan. 24, 2019

(65) Prior Publication Data
US 2021/0142498 A1     May 13, 2021

Related U.S. Application Data

(60) Provisional application No. 62/489,115, filed on Apr. 24, 2017.

(51) Int. Cl.
*G06T 7/55*       (2017.01)
*G16C 20/20*     (2019.01)
(Continued)

(52) U.S. Cl.
CPC ............... *G06T 7/55* (2017.01); *G06T 17/00* (2013.01); *G16B 15/00* (2019.02); *G16C 20/20* (2019.02);
(Continued)

(58) Field of Classification Search
CPC . G06T 7/55; G06T 17/00; G06T 2207/10061; G06T 2207/20056;
(Continued)

(56) References Cited

U.S. PATENT DOCUMENTS

| | | |
|---|---|---|
| 7,418,693 B1 | 8/2008 | Gennari et al. |
| 7,958,063 B2 | 6/2011 | Long et al. |

(Continued)

FOREIGN PATENT DOCUMENTS

| | | |
|---|---|---|
| JP | 2017-067746 A | 4/2017 |
| WO | WO 2003/105675 A2 | 12/2003 |

OTHER PUBLICATIONS

Aebeláez et al., "Experimental evaluation of support vector machine-based and correlation-based approaches to automatic particle selection," Journal of Structural Biology, 2011, 175, 319-328.

(Continued)

*Primary Examiner* — Christopher M Brandt
(74) *Attorney, Agent, or Firm* — Michael Best & Friedrich LLP

(57) ABSTRACT

Methods and systems are described for digitally reconstructing an unknown 3D structure of a target molecule using orthogonal extension. A plurality of 2D images of the target molecule are captured by an imaging system. An estimated low-order moment of the unknown 3D structure (e.g., a covariance matrix) is calculated based on the 2D images. A homologous molecule having a known 3D structure is identified and at least one expansion coefficient of the known structure of the homologous molecule is determined. At least (Continued)

one estimated expansion coefficient for the unknown structure is calculated based at least in part on the estimated low order moment of the unknown structure and the at least one expansion coefficient of the known structure. An estimated 3D reconstruction of the target molecule is then generated based on the at least one estimated expansion coefficient for the unknown structure of the target molecule.

15 Claims, 9 Drawing Sheets

(51) Int. Cl.
*G16B 15/00* (2019.01)
*G06T 17/00* (2006.01)
(52) U.S. Cl.
CPC ............... *G06T 2207/10061* (2013.01); *G06T 2207/20056* (2013.01)
(58) Field of Classification Search
CPC .......... G16C 20/20; G16B 15/00; G01N 1/42; C07K 14/00
See application file for complete search history.

(56) References Cited

U.S. PATENT DOCUMENTS

| | | | |
|---|---|---|---|
| 8,577,171 | B1 | 11/2013 | Mollon |
| 9,747,706 | B2* | 8/2017 | Teshigawara ......... G06T 11/006 |
| 2005/0119835 | A1* | 6/2005 | Kita ....................... G16B 15/00 702/19 |
| 2007/0197894 | A1* | 8/2007 | Jo ....................... G01N 21/6458 600/407 |
| 2008/0212880 | A1 | 9/2008 | Homman et al. |
| 2009/0226096 | A1 | 9/2009 | Namai et al. |
| 2010/0010946 | A1 | 1/2010 | De Winter et al. |
| 2016/0267315 | A1 | 9/2016 | Roth |
| 2017/0103161 | A1 | 4/2017 | Brubaker et al. |

OTHER PUBLICATIONS

Bai et al., "How cryo-EM is revolutionizing structural biology," Trends in Biochemical Sciences, 2015, 40(1):49-57.
Barnett et al., "Rapid Solution of the Cryo-EM Reconstruction Problem by Frequency Marching," SIAM J. Imaging Sciences, 2017, 10(3):1170-1195.
Bendory et al., "Bispectrum inversion with application to multireference alignment," IEEE Transactions on Signal Processing, 2018, 66(4):1037-1050.
Bhamre et al., "Denoising and covariance estimation of single particle cryo-EM images," Journal of Structural Biology, 2016, 195(1):72-81.
Bhamre et al., "Orthogonal Matrix Retrieval in Cryo-Electron Microscopy," 12th IEEE International Symposium on Biomedical Imaging, 2015, pp. 1048-1052.
Bhamre et al., "Anisotropic twicing for single particle reconstruction using autocorrelation analysis", https://arxiv.org/abs/1704.07969 (2017) 34 pages.
Boumal et al., "Manopt, a Matlab toolbox for optimization on manifolds," Journal of Machine Learning Research, 2014, 15:1455-1459.
Burvall et al., "Phase retrieval in X-ray phase-contrast imaging suitable for tomography," Optics express, 2011, 19(11), 10359-10376.
Chen et al., "High-resolution noise substitution to measure overfitting and validate resolution in 3D structure determination by single particle electron cryomicroscopy," Ultramicroscopy, 2013, 135, 24-35.
Chen et al., "SIGNATURE: A single-particle selection system for molecular electron microscopy," Journal of Structural Biology, 2007, 157, 168-173.
Cheng, "Random Matrices in High-dimensional Data Analysis," Princeton University Doctoral Dissertation, 2013, 136 pages.
Cowtan, K., (2014). Kevin cowtan's picture book of fourier transforms. <http://www.ysbl.york.ac.uk/~cowtan/fourier/fourier.html>.
Cristianini et al., (2000). An Introduction to Support Vector Machines: And Other Kernel-based Learn-ing Methods. New York, NY, USA: Cambridge University Press.
Frank et al., "Automatic selection of molecular images from electron micrographs," Ultramicroscopy, 1983-1984, 12(3): 169-175.
Gao et al., "TRPV1 structures in nanodiscs reveal mechanisms of ligand and lipid action," Nature, 2016, 534(5):347-351.
Glaeser, "Historical background: why is it important to improve automated particle selection methods?" Journal of Structural Biology, 2004, 145(1-2):15-18.
Goncharov, "Integral geometry and three-dimensional reconstruction of randomly oriented identical particles from their electron microphotos," Acta Applicandae Mathematica, 1988, 11(3):199-211.
Grigorieff, "FREALIGN: High-resolution refinement of single particle structures," Journal of Structural Biology, 2007, 157(1):117-125.
Harauz et al., "Automatic selection of macromolecules from electron micrographs by component labelling and symbolic processing," Ultramicroscopy, 1989, 31(4):333-344.
Heimowitz et al., "APPLE Picker: Automatic Particle Picking, a Low Effort Cryo-EM framework," Journal of Structural Biology, Nov. 2018, 204(2):215-227.
Henderson, "Realizing the potential of electron cryo-microscopy," Quarterly Reviews of Biophysics, 2004, 37(1):3-13.
Hoang et al., "gEMpicker: a highly parallel GPU-accelerated particle picking tool for cryo-electron microscopy," BMC Structural Biology, 2013, 13:25.
Hosseinizadeh et al., "Single-particle structure determination by X-ray free-electron lasers: Possibilities and challenges," Structural dynamics, 2015, 2(4):041601.
International Search Report and Written Opinion for Application No. PCT/US2018/029452 dated Dec. 31, 2018 (11 pages).
International Search Report and Written Opinion for Application No. PCT/US2018/037375 dated Nov. 1, 2019 (11 pages).
Iudin et al., "EMPIAR: A public archive for raw electron microscopy image data," Nature Methods, 2016, 13(5):387-388.
Kam et al., "Three-dimensional reconstruction of the shape of human wart virus using spatial correlations," Ultramicroscopy, 1985, 17(3):251-262.
Kam, "Determination of Macromolecular Structure in Solution by Spatial Correlation of Scattering Fluctuations," Macromolecules, 1977, 10(5):927-934.
Kam, "The reconstruction of structure from electron micrographs of randomly oriented particles," Journal of Theoretical Biology, 1980, 82(1):15-39.
Kecman, V. (2001). Learning and Soft Computing: Support Vector Machines, Neural Networks, and Fuzzy Logic Models. Cambridge, MA, USA: MIT Press.
Keller, "Closest Unitary, Orthogonal and Hermitian Operators to a Given Operator," Mathematics Magazine, 1975, 48(4):192-197.
Klein, F. (1914). Lectures on the icosahedron and the solution of equations of the fifth degree. London. 16, pp. 288-289.
Klug et al., "Three-dimensional Image Reconstruction from the Viewpoint of information Theory," Nature, 1972, 238(5365):435-440.
Kühlbrandt, "Biochemistry. The resolution revolution," Science, 2014, 343(6178):1443-1444.
Langlois et al., "Automated particle picking for low-contrast macromolecules in cryo-electron microscopy," Journal of Structural Biology, 2014, 186(1):1-7.
Liu et al., "Phase retrieval in x-ray imaging based on using structured illumination," Physical Review A, 2008, 78, 023817.
Ludtke et al., "Eman: Semiautomated software for high-resolution single-particle reconstructions," J Struct Biol, 1999, 128(1):82-97.

(56) References Cited

OTHER PUBLICATIONS

Main, "A theoretical comparison of the [beta],[gamma]' and 2Fo-Fc syntheses," Acta Crystallographica Section A, 1979, 35(5):779-785.
Marabini et al., "Xmipp: An Image Processing Package for Electron Microscopy," Journal of Structural Biology, 1996, 116(1):237-240.
Nicholson et al., "Review: Automatic particle detection in electron microscopy," Journal of Structural Biology, 2001, 133(2-3):90-101.
Ogura et al., "Automatic particle pickup method using a neural network has high accuracy by applying an initial weight derived from eigenimages: a new reference free method for single-particle analysis," Journal of Structural Biology, 2004, 145, 63-75.
Pettersen et al., "UCSF Chimera—a visualization system for exploratory research and analysis," Journal of Computational Chemistry, 2004, 25(13):1605-1612.
Pfeiffer et al., "Phase retrieval and differential phase-contrast imaging with low-brilliance X-ray sources," Nat Phys, 2006, 2(4):258-261.
Punjani et al., "cryoSPARC: algorithms for rapid unsupervised cryo-EM structure determination," Nature Methods, 2017, 14:290-296.
Radermacher et al., "Three-dimensional structure of the large ribosomal subunit from *Escherichia coli*," EMBO J, 1987, 6(4):1107-1114.
Roseman, "FindEM—a fast, efficient program for automatic selection of particles from electron micrographs," Journal of Structural Biology, 2004, 145(1-2):91-99.
Rossmann et al., "The detection of sub-units within the crystallographic asymmetric unit," Acta Crystallographica, 1962, 15(1):24-31.
Rossmann, "Molecular replacement—historical background," Acta Crystallographica Section D, 2001, 57(10):1360-1366.
Saldin et al., "Structure of isolated biomolecules obtained from ultrashort x-ray pulses: exploiting the symmetry of random orientations," Journal of Physics: Condensed Matter, 2009, 21(13):134014.
Salzman, "A method of general moments for orienting 2D projections of unknown 3D objects," Computer Vision, Graphics, and Image Processing, 1990, 50(2):129-156.
Scapin, "Molecular replacement then and now," Acta Crystallographica Section D, 2013, 69(11):2266-2275.
Scheres et al., "Prevention of overfitting in cryo-EM structure determination," Nature Methods, 2012, 9(9):853-854.
Scheres, "RELION: Implementation of a Bayesian approach to cryo-EM structure determination," Journal of Structural Biology, 2012, 180(3):519-530.
Scheres, "Semi-automated selection of cryo-EM particles in RELION-1.3," Journal of Structural Biology, 2015, 189(2):114-122.
Schölkopf, B., & Smola, A. J. (2001). Learning with Kernels: Support Vector Machines, Regularization, Optimization, and Beyond. Cambridge, MA, USA: MIT Press.
Shaikh et al., "SPIDER image processing for single-particle reconstruction of biological macromolecules from electron micrographs," Nature Protocols, 2008, 3(12):1941-1974.
Shatsky et al., "A method for the alignment of heterogeneous macromolecules from electron microscopy," Journal of Structural Biology, 2009, 166(1):67-78.
Sigworth, "Classical detection theory and the cryo-EM particle selection problem," Journal of Structural Biology, 2004, 145, 111-122.
Singer et al., "Detecting consistent common lines in cryo-EM by voting," Journal of Structural Biology, 2009, 169(3):312-322.
Singer et al., "Three-dimensional structure determination from common lines in cryo-EM by eigenvectors and semidefinite programming," SIAM Journal on Imaging Sciences, 2011, 4(2):543-572.
Spahn et al., "Exploring conformational modes of macromolecular assemblies by multiparticle cryo-EM," Current Opinion in Structural Biology, 2009, 19(5):623-631.
Starodub et al., "Single-particle structure determination by correlations of snapshot X-ray diffraction patterns," Nature Communications, 2012, 3, Article No. 1276.
Suykens et al., "Least Squares Support Vector Machine Classifiers," Neural Process. Lett., 1999, 9, 293-300.
Tang et al., "EMAN2: An extensible image processing suite for electron microscopy," Journal of Structural Biology, 2007, 157(1):38-46.
Tukey, J. W. (1977). Exploratory Data Analysis. Addison-Wesley.
Vainshtein, B. & Goncharov, A., "Determining the spatial orientation of arbitrarily arranged particles given their projections," Dokl. Acad. Sci. USSR 287, n. 5, 1131-1134 (1986). English translation: Soviet Physics Doklady, 31, 278.
Van Heel et al., "Use of multivariate statistics in analysing the images of biological macromolecules," Ultramicroscopy, 1981, 6(2):187-194.
Van Heel, "Angular reconstitution: A posteriori assignment of projection directions for 3D reconstruction," Ultramicroscopy, 1987, 21(2):111-123.
Van Heel, "Detection of objects in quantum-noise-limited images," Ultramicroscopy, 1982, 7(4):331-341.
Van Heel, "Multivariate statistical classification of noisy images (randomly oriented biological macromolecules)," Ultramicroscopy, 1983, 13(1):165-184.
Vapnik, V. N. (1995). The Nature of Statistical Learning Theory. New York, NY, USA: Springer-Verlag New York, Inc.
Voss et al.,"DoG picker and TiltPicker: Software tools to facilitate particle selection in single particle electron microscopy," Journal of Structural Biology, 2009, 166(2):205-213.
Wang et al., DeepPicker: a deep learning approach for fully automated particle picking in cryo-EM, Journal of Structural Biology, 2016, 195(3):325-336.
Zhao et al., "Fast Steerable Principal Component Analysis," IEEE Transactions on Computational Imaging, 2016, 2(1):1-12.
Zhao et al., "Fourier-Bessel rotational invariant eigenimages," J. Opt. Soc. Am. A, 2013, 30(5):871-877.
Zhao et al., "Rotationally Invariant Image Representation for Viewing Direction Classification in Cryo-EM", Journal of Structural Biology, 2014, 186(1):153-166.
Zhou, "Multireference Alignment via Semidefinite Programming", Princeton University Senior Thesis (2013) 12 pages.
Zhu et al., "A deep convolutional neural network approach to single-particle recognition in cryo-electron microscopy," BMC Bioinformatics, 2017, 18, Article No. 348.
Zhu et al., "Automatic particle detection through efficient hough transforms," IEEE Transactions on Medical Imaging, 2003, 22, 1053-1062.
Zhu et al., "Automatic particle selection: results of a comparative study," Journal of Structural Biology, 2004, 145, 3-14.
European Patent Office Extended Search Report for Application No. 18911417.6 dated Jan. 29, 2021 (7 pages).
Zhang et al., "A Two-Phase Improved Correlation Method for Automatic Particle Selection in Cryo-EM", IEEE/ACM Transactions on Computational Biology and Bioinformatics, vol. 14, No. 2, 2017, pp. 316-325.
Chinese Patent Office First Office Action for Application No. 201880046702.X dated Sep. 3, 2021 (24 pages including English translation).

* cited by examiner

ANISOTROPIC TWICING FOR SINGLE PARTICLE RECONSTRUCTION USING AUTOCORRELATION ANALYSIS

RELATED APPLICATIONS

This application is the U.S. national stage entry, under 35 U.S.C. § 371, of International Application Number PCT/US2018/029152, filed Apr. 24, 2018, which claims the benefit of U.S. Provisional Patent Application No. 62/489,115, filed Apr. 24, 2017, entitled "ANISOTROPIC TWICING FOR SINGLE PARTICLE RECONSTRUCTION USING AUTOCORRELATION ANALYSIS," the entire contents of each of which are incorporated herein by reference.

STATEMENT REGARDING FEDERALLY SPONSORED RESEARCH OR DEVELOPMENT

This invention was made with government support under Grant No. GM-090200 awarded by the National Institutes of Health and Grant No. FA9550-12-1-0317 awarded by the Air Force Office of Scientific Research. The government has certain rights in the invention.

BACKGROUND

The present invention relates to systems and methods for determining a structure of a molecule using an imaging system such as, for example, x-ray free electron lasers and cryo-electron microscopy (cryo-EM).

SUMMARY

The three-dimensional structure of an object—for example, a molecule—can be determined using imaging techniques, such as, for example, cryo-electron microscopy (cyro-EM) in which multiple 2D images of the object are captured and then processed to generate a three-dimensional reconstruction of the object. In some implementations, the imaging system defines the 3D structure of the object using Cartesian coordinates while, in other implementations, the 3D structure of the object is defined formulaically, for example, using a function or a collection of functions (e.g., radial functions).

In some situations, an imaging system might be utilized to determine the 3D structure of a molecule that has been modified in some way from a known structure of the molecule (or a known structure of a similar molecule). For example, the 3D structure of a molecule may be changed when the molecule binds to another molecule. One option for determining the 3D structure of the modified molecule would be to capture a sufficient number of 2D images in order to generate a reconstruction of the 3D structure. However, in some situations, this is type of reconstruction can require a large number of 2D images and computational resources. Particularly in situations where many different modifications of the molecule structure are being analyzed, this process can take too long and can hinder/limit research progress.

In various embodiments, the invention described in this disclosure provides a technique for reconstructing an unknown 3D structure of a molecule based on a combination of 2D image data for the molecule and a previously determined 3D structure of a homologous (i.e., similar) molecule. Instead of capturing enough 2D images to determine the structure of the new molecule on its own, the methods and system described herein capture only enough 2D images of the molecule in order to determine how the molecule is different from the homologous molecule. As a result, fewer 2D images of the molecule are required and the computational load (and, in turn, processing time) for determining the 3D structure of the molecule is also reduced.

In some implementations, the coefficients of the function defining the 3D structure of a homologous molecule are known (e.g., based on previously captured and reconstructed image data). Based on the assumption that the 3D structure of the new molecule is similar to the 3D structure of the homologous molecule, the coefficients of a function defining the 3D structure of the new molecule will be similar/close to the coefficients of the function defining the 3D structure of the homologous molecule. Accordingly, in some implementations, the invention provides methods and systems for determining an estimated difference between the coefficients of the function defining the 3D structure of the new molecule and the coefficients of the function defining the 3D structure of the homologous molecule.

In some embodiments, the system is configured to compute the first two moments from the image data of a plurality of 2D images of the new molecule. The computed first moment is indicative of the average image and the second moment is indicative of the 2D covariance matrix of the image data. The 2D covariance matrix is indicative of the correlation between pixel values across the image in all image of the plurality of images. The covariance matrix computed from the 2D image data gives information about the 3D structure. However, in some implementations, the covariance matrix alone is not enough to reconstruct the 3D structure. Instead, the system is configured to calculate the estimated expansion coefficients for the unknown 3D structure of the new molecule based on the 2D covariance matrix and the expansion coefficients of the known 3D structure of the homologous molecule.

In one embodiment, the invention provides a method for generating an estimated 3D structure of a target molecule based on a plurality of 2D images of the target molecule and a stored representation of a known 3D structure of a homologous molecule. First and second order moments of the 3D structure of the target molecule are calculated based on the captured 2D images. Expansion coefficients for a known 3D structure of a homologous molecule are determined based on data stored to a memory. Estimated expansion coefficients of the unknown 3D structure of the target molecule are then calculated based on the expansion coefficients from the homologous molecule and at least the second order moment calculated for the unknown 3D structure. After the estimated expansion coefficients for the unknown 3D structure are estimated, an estimated 3D structure of the target molecule is generated and, in some embodiments, a visual representation of the estimated 3D structure is output on a display screen.

In another embodiment, the invention provides a method for generating an estimated 3D structure of a target molecule. A plurality of 2D raw cryo-EM images of the target molecule are captured and the 2D image data is expanded in a truncated steerable basis (e.g., Fourier-Bessel basis). A covariance matrix for the 3D structure of the target molecule is then estimated by applying a steerable principal component analysis and estimated autocorrelation matrices are calculated from the estimated covariance matrix. The spherical harmonic expansion coefficients for the 3D structure of the target molecule are then calculated up to one or more missing orthogonal matrices. The 3D Fourier transform of a homologous molecule is calculated in a truncated spherical harmonic basis from a known 3D structure of a homologous molecule stored to a memory. An estimation of the missing orthogonal matrices for the 3D structure of the target molecule is then calculated using orthogonal extension based in part on the 3D Fourier transform of the homologous molecule. The spherical harmonic expansion coefficients of the unknown 3D structure of the target molecule are then recovered based at least in part on the estimated spherical harmonic expansion coefficients calculated from the 2D image data and the estimated missing orthogonal matrices. The estimated 3D structure of the target molecule is then generated based on the recovered spherical harmonic expansion coefficients and, in some embodiments, a visual representation of the estimated 3D structure of the target molecule is output on a display screen.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
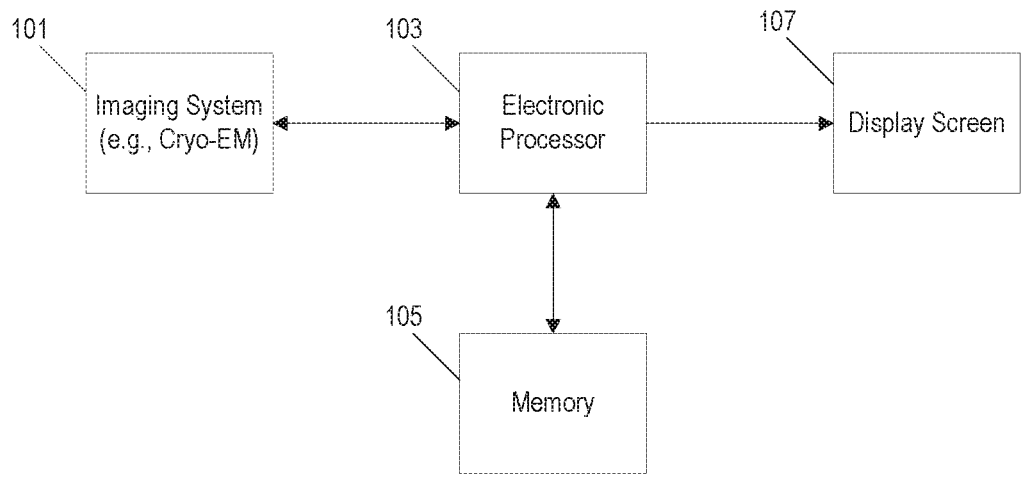
FIG. 1 is a block diagram of a system for determining a 3D structure of a target molecule according to one embodiment.

FIG. 1 illustrates an example of a system for generating reconstructions of the 3D structure of an object—for example, a molecule. An imaging system 101 captures image data of the object. The imaging system 101 may include, for example, a cryo-electron microscopy (cryo-EM) imaging system configured to capture a plurality of 2D projection images of the object (e.g., a target molecule) from a plurality of different viewing angles. Image data captured by the imaging system 101 is transmitted to an image processing system including and electronic processor 103 and a non-transitory computer-readable memory 105. The electronic processor 103 is configured to executed instructions stored on the memory 105 to provide system functionality such as, for example, described herein. The electronic processor 103 is configured to process the image data captured by and received from the imaging system 101 in order to reconstruct the 3D structure of the object (e.g., the target molecule). The electronic processor 103 is also configured to store the reconstruction of the 3D structure of the object to the memory 105 and, in some implementations, to store other reconstructions of other 3D structures to the memory 105. Similarly, the electronic processor 103 is communicatively coupled to a display screen 107 and is configured to selectively output a visual representation of a reconstruction of a 3D structure to the display screen 107 causing the visual representation to be shown on the display screen 107.

In some implementations, the system of FIG. 1 is configured to capture a sufficient number of 2D images of a target object such that a 3D reconstruction of the structure of the object can be generated entirely from the 2D image data captured by the imaging system 101. Alternatively or additionally, in some implementations, the system of FIG. 1 may be configured to generate a 3D reconstruction of the structure of the object based on a smaller set of 2D images and information derived from another 3D structure that is already stored on the memory 105. For example, the system of FIG. 1 may be configured to access a reconstruction of a 3D structure stored to memory that is similar to the target object (e.g., a homologous object). Instead of capturing and processing new images in order to reconstruct the entire 3D structure of the target object, the system is instead configured to capture and process new images of the target object in order to identify differences between the target object and the homologous object.

Figure 2:
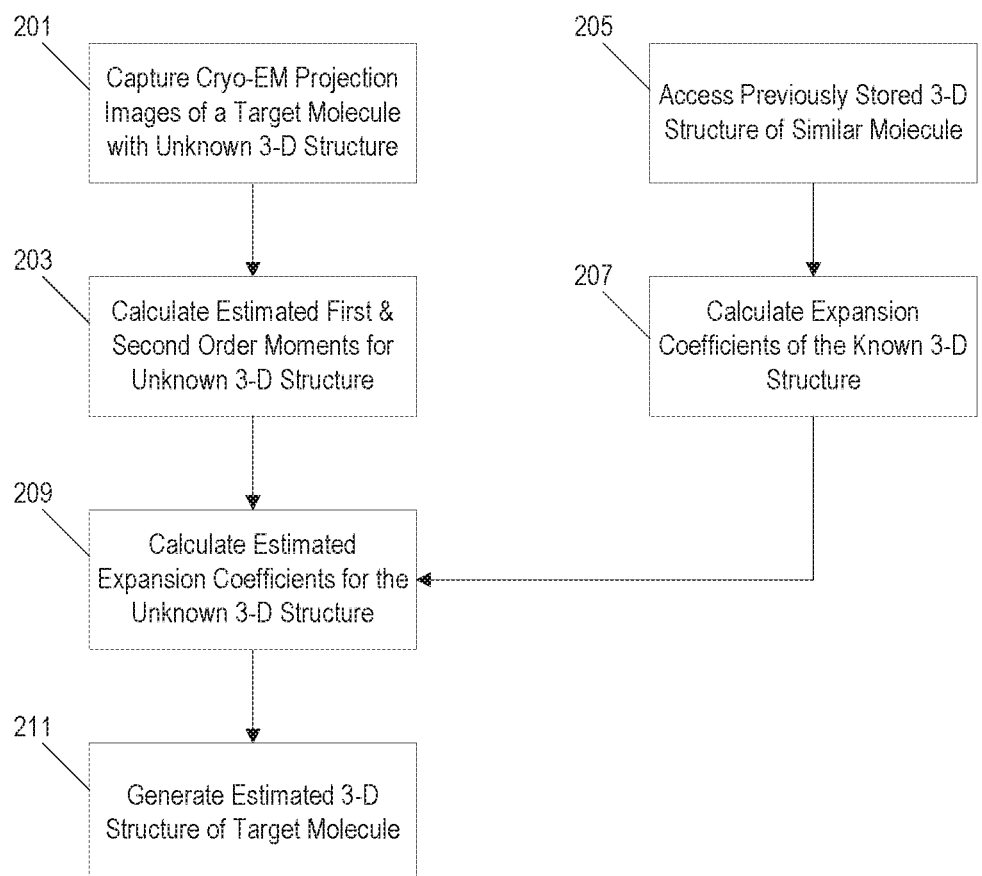
FIG. 2 is a flowchart of a method for generating an estimated 3D structure of a target molecule based on a plurality of 2D images of the target molecule and a known 3D structure of a homologous molecule using the system of FIG. 1.

FIG. 2 is one example of a method for determining an estimated 3D structure of a target molecule using the system of FIG. 1. A plurality of 2D cryo-EM projection images of the target molecule are captured using the imaging system 101 (step 201). The system of FIG. 1 then processes the captured image data to calculate a first order moment and a second order moment for the unknown 3D structure of the target molecule (step 203). In some implementations, the first order moment is an average image calculated from the raw image data captured by the imaging system and, in some implementations, the second order moment is a 2D covariance matrix indicating a correlation between pixel values across the image in all of the images of the target molecule captured by the imaging system 101. The 2D covariance matrix provides information about the 3D structure of the target molecule. However, the 2D covariance matrix alone does not provide enough data in order to reconstruct the entire 3D structure of the target molecule. Instead, the system access a previously stored 3D structure of a similar molecule (e.g., a homologous molecule) from the memory 105 (step 205) and calculates expansion coefficients of the known 3D structure (step 207). Based on the expansion coefficients for the known 3D structure of the homologous molecule and the second order moment calculated for the unknown 3D structure of the target molecule, the system calculates estimated expansion coefficients for the unknown 3D structure of the target molecule (step 209). Based on the estimated expansion coefficients, the system generates an estimated reconstruction of the 3D structure of the target molecule (step 211). The estimated reconstruction is then stored to memory and a visual representation of the estimated reconstruction of the 3D structure of the target molecule is output on the display screen 107.

The missing phase problem in crystallography entails recovering information about a crystal structure that is lost during the process of imaging. In X-ray crystallography, the measured diffraction patterns provide information about the modulus of the 3D Fourier transform of the crystal. The phases of the Fourier coefficients need to be recovered by other means, in order to reconstruct the 3D electron density map of the crystal. One method to solve the missing phase problem is Molecular Replacement (MR), which relies on a previously solved homologous structure which is similar to the unknown structure. The unknown structure is then estimated using the Fourier magnitudes of its diffraction data, along with phases from the homologous structure.

The missing phase problem can be formulated mathematically using matrix notation that enables generalization as follows. Each Fourier coefficient A is a complex-valued scalar, i.e., $A \in \mathbb{C}^{1 \times 1}$ that we wish to estimate, given measurements of $C = A A^*$ ($A^*$ denotes the complex conjugate transpose of A, i.e., $A_{ij}^* = \overline{A_{ij}}$), corresponding to the Fourier squared magnitudes, and B corresponds to a previously solved homologous structure such that $A = B + E$, where E is a small perturbation. We denote an estimator of A as $\hat{A}$. There are many possible choices for such an estimator. One such choice is the solution to the least squares problem $$\hat{A}_{LS} = \arg_A \min \|A - B\|_F, \text{subject to } A A^* = C \quad (1)$$

where $\|\cdot\|_F$ denotes the Frobenius norm. However, $\hat{A}_{LS}$ does not reveal the correct relative magnitude of the unknown part of the crystal structure, and the recovered magnitude is about half of the actual value. As a magnitude correction scheme, it was empirically found that setting the magnitude to be twice the experimentally measured magnitude minus the magnitude of the homologous structure has the desired effect of approximately resolving the issue. That is, the estimator $2\hat{A}_{LS} - B$ is used instead. This procedure is referred to as twicing.

In this disclosure, we consider the following problem: How to estimate $A \in \mathbb{R}^{N \times D}$ (or $\mathbb{C}^{N \times D}$) from C and B, where $C = A A^*$ and $A = B + E$ for matrix E of small magnitude? When $N = D$, the result described below for an asymptotically consistent estimator of A is given by $\hat{A}_{AT} = B + UWU^*(\hat{A}_{LS} - B)$.

The motivation to study this problem is 3D structure determination in single particle reconstruction (SPR) without estimating the viewing angle associated with each image. Although the examples discussed in this disclosure focus on cryo-electron microscopy (cryo-EM), the methods and systems can also be applied to SPR using other imaging techniques including, for example, x-ray free electron lasers (XFEL). In SPR using XFEL, short but intense pulses of x-rays are scattered from the molecule. The measured 2D diffraction patterns in random orientations are used to reconstruct the 3D diffraction volume by an iterative refinement procedure, akin to the approach in cryo-EM.

Some of the examples discussed below utilized orthogonal extension (OE) in cryo-EM that combines ideas from MR and Kam's autocorrelation analysis for the purpose of 3D homology modeling, that is, for reconstruction of an unknown complex directly from its raw, noisy images when a previously solved similar complex exists. In SPR using cryo-EM, the 3D structure of a macromolecule is reconstructed from its noisy, contrast transfer function (CTF) affected 2D projection images. Individual particles images are picked from micrographs, preprocessed, and used in further parts of the cryo-EM pipeline to obtain the 3D density map of the macromolecule. Algorithms such as RELON, XMIPP, SPIDER, EMAN2, FREALIGN refine a starting 3D structure using noisy 2D projection imagines. The result of the refinement procedure is often dependent on the choice of the initial model. It is therefore important to have a procedure to provide a good starting model for refinement. Also, a high quality starting model may significantly reduce the computational time associated with the refinement procedure. Such a high quality starting model can be obtained using OE. The main computational component of autocorrelation analysis is the estimation of the covariance matrix of the 2D images. This computation requires only a single pass over the experimental images. Autocorrelation analysis is therefore much faster than iterative refinement, which typically takes many iterations to converge. In fact, the computational cost of autocorrelation analysis is even lower than that of a single refinement iteration, as the latter involves comparison of image pairs (noisy raw images with volume projections). OE can also be used for the purpose of model validation, being a complementary method for structure prediction.

In some implementations, OE predicts the structure directly from the raw, noisy images without any averaging. The method is analogous to MR in x-ray crystallography for solving the missing phase problem. In OE, the homologous structure is used for estimating the missing orthogonal matrices associated with the spherical harmonic expansion of the 3D structure in reciprocal space. It is important to note that the missing orthogonal matrices in OE are not associated with the unknown pose of the particles, but with the spherical harmonics expansion coefficients. The missing coefficient matrices are, in general, rectangular of size N×D, which serves as the motivation to extend twicing to the general case of finding an estimator when $(N,D) \neq (1,1)$.

Figure 3A:
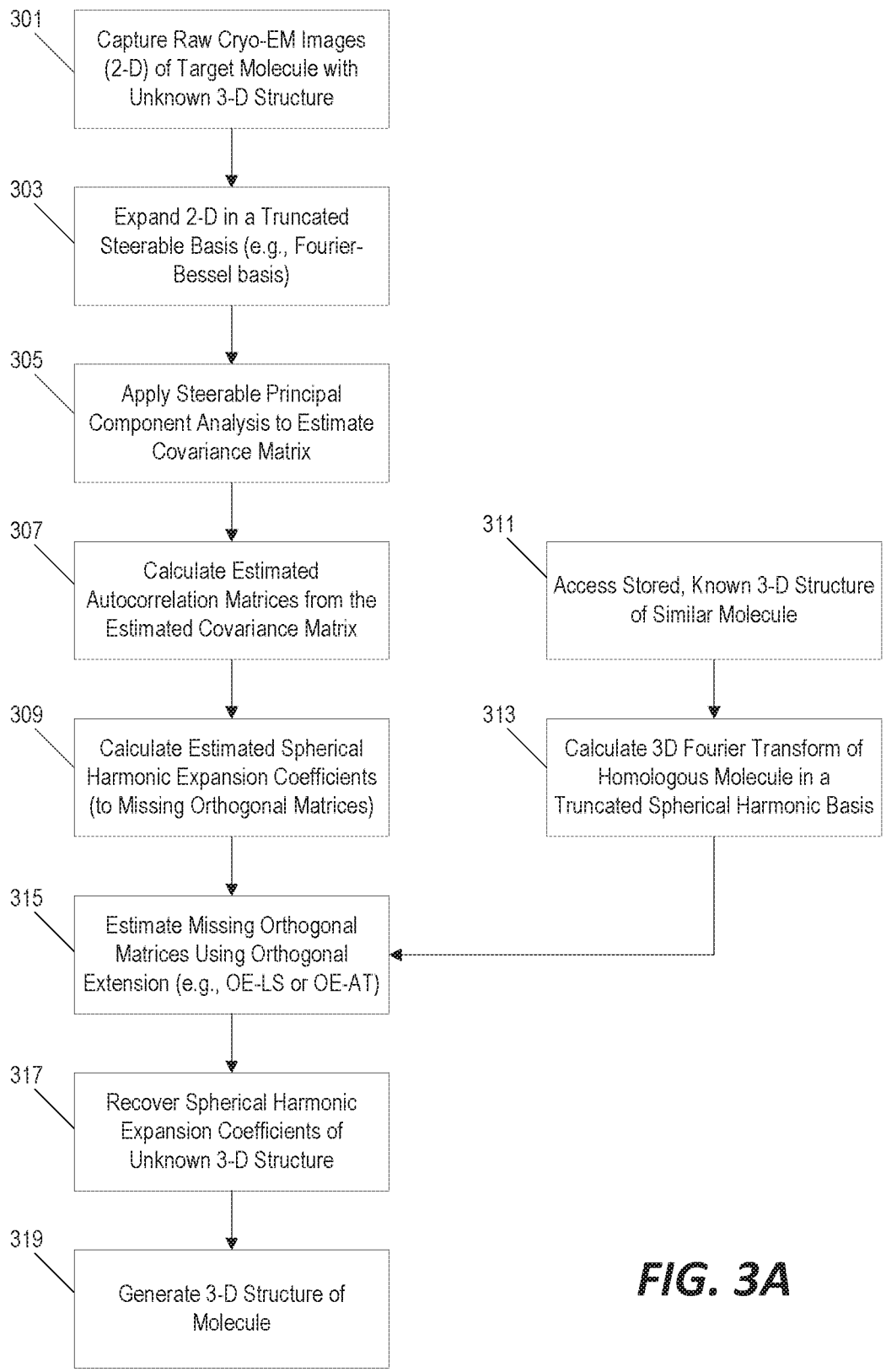
FIG. 3A is a flowchart of another method for generating an estimated 3D structure of a target molecule by recovering spherical harmonic expansion coefficients of the 3D structure of the target molecule from a plurality of 2D images of the target molecule and a 3D Fourier transform of a known 3D structure of a homologous molecule using the system of FIG. 1.

FIG. 3A illustrates a method for estimating a 3D structure of a target molecule using orthogonal extension. First, a plurality of raw 2D cryo-EM projection images are captured of a target molecule with an unknown 3D structure (step 301). Next, the 2D images are expanded in a truncated steerable basis such as Fourier-Bessel basis (step 303). The system then applies a steerable principal component analysis to estimate the covariance matrix of the underlying clean images and their in-plane rotations (step 305). The autocorrelation matrices of the unknown 3D structure are then estimated from the covariance matrix, for example, using Kam's theory (step 307). The Cholesky decomposition of the autocorrelation matrices is then computed to estimate the spherical harmonic expansion coefficients of the unknown 3D structure of the target molecule up to the missing orthogonal matrices (step 309). In order to estimate/recover the missing orthogonal matrices for the unknown 3D structure of the target molecule, a reconstruction of a similar molecule (e.g., a homologous molecule) with a known 3D structure is accessed from memory (step 311) and the 3D Fourier transform of the homologous molecule is computed in a truncated spherical harmonic basis (e.g., spherical-Bessel) (step 313). Orthogonal extension is then applied (as discussed in further detail below) to estimate the missing orthogonal matrices (step 315) and the spherical harmonic expansion coefficients of the unknown 3D structure of the target molecule are recovered (step 317). Finally, based on the recovered spherical harmonic expansion coefficients, a reconstruction of the 3D structure of the target molecule is generated (step 319). In some implementations, the reconstruction of the 3D structure is stored to memory and/or a visual representation of the reconstruction of the 3D structure is output on a display screen.

"Orthogonal Retrieval" is an approach for 3D homology modeling based on Kam's theory. Orthogonal Retrieval can be regarded as a generalization of the MR method from x-ray crystallography to cryo-EM. Let $\Phi_A: \mathbb{R} \to \mathbb{R}$ be the electron scattering density of the unknown structure, and let $F(\Phi_A): \mathbb{R}^3 \to \mathbb{C}$ be its 3D Fourier transform. Consider the spherical harmonics expansion of $F(\Phi_A)$ $$F(\Phi_A)(k,\theta,\varphi) = \sum_{l \geq 0}^{\infty} \sum_{m=-l}^{l} A_{lm}(k) Y_l^m(\theta,\varphi) \tag{2}$$

where k is the radial frequency and $Y_l^m$ are the real spherical harmonics. The autocorrelation matrices $$C_l(k_1,k_2) = \sum_{m=-l}^{l} A_{lm}(k_1) \overline{A_{lm}(k_2)}, l=0,1,\ldots \tag{3}$$

can be estimated from the covariance matrix of the 2D projection images whose viewing angles are uniformly distributed over the sphere. This can be achieved with both clean as well as noisy images, as long as the number of noisy images is large enough to allow estimation of the underlying population covariance matrix of the clean images to the desired level of accuracy. The decomposition (equation 3) suggests that the $l^{th}$ order autocorrelation matrix $C_l$ has a maximum rank of 2l+1, and the maximum rank is even smaller in the presence of symmetry.

While equation (2) holds true if the molecule is represented to infinitely high resolution, in practice the images are sampled on a finite pixel grid and information cannot be recovered beyond the Nyquist frequency. In addition, the molecule is compactly support in $\mathbb{R}^3$, d a the support size can also be estimated from the images. It therefore follows to expand the volume in a truncated basis of spherical Bessel functions or 3D prolates. This leads to $$F(\Phi_A)(k,\theta,\varphi) = \sum_{l=0}^{L} \sum_{m=-l}^{l} A_{lm}(k) Y_l^m(\theta,\varphi), l=0,1,\ldots,L \tag{4}$$

where the truncation L is based on the resolution limit that can be achieved by the reconstruction. Our specific choice of L is described after equation (8) below. We can expand $A_{lm}(k)$ in a truncated basis of radial functions, chosen here as the spherical Bessel functions, as follows:

$$A_{lm}(k) = \sum_{s=1}^{S_l} a_{lms} j_{ls}(k) \tag{5}$$

Here the normalized spherical Bessel functions are $$A_{lm}(k) = \frac{1}{c\sqrt{\pi}|j_{l+1}(R_{l,s})|} j_l\left(R_{l,s} \frac{k}{c}\right), 0 < k < c, s = 1, 2, \ldots, S_l \tag{6}$$

where c is the bandlimit of the images, and $R_{l,s}$ is the $s^{th}$ positive root of the equation $j_l(x)=0$. The functions $j_{ls}$ are normalized such that $$\int_0^c j_{ls}(k) j_{ls}^*(k) k^2 dk = 1 \tag{7}$$

The number of the radial basis functions $S_l$ in equation (5) is determined using the Nyquist criterion. We assume that the 2D images, and hence the 3D volume are compactly supported on a disk of radius R and have a bandlimit of $0 < c \leq 0.5$. We require that the maximum of the inverse Fourier transform of the spherical Bessel function and its first zero after this maximum are both inside the sphere of compact support radius R. The truncation limit S in equation (5) is then defined by the sampling criterion as the largest integers that satisfies $$R_{l,(s+1)} \leq 2\pi cR \tag{8}$$

L in equation (4) is the largest integer l for which equation (8) has only one solution, that is $S_l$ in equation (5) is at least 1. Each $C_l$ is a matrix of size $S_l \times S_l$ when using the representation of equation (5) in equation (3). $S_l$ is a monotonically decreasing function of l with approximately linear decay that we compute numerically. In matrix notation, equation (3) can be written as $$C_l = A_l A_l^* \tag{9}$$

where $A_l$ is a matrix of size $S_l \times (2l+1)$, with $A_l(s,m) = a_{lms}$ in equation (5). From equation (9), we note that $A_l$ can be obtained from the Cholesky decomposition of $C_l$ up to a unitary matrix $U_l \in U(2l+1)$ (the group of unitary matrices of size $(2l+1) \times (2l+1)$). Since $\Phi_A$ is real-valued, one can show using properties of its Fourier transform together with properties of the real spherical harmonics, that $A_{lm}(k)$ (and hence $A_l$) is real for even l and purely imaginary for odd l. So $A_l$ is unique up to an orthogonal matrix $O_l \in O(2l+1)$ (the group of unitary matrices of size $(2l+1) \times (2l+1)$). Determining $O_l$ is an orthogonal retrieval problem.

If $S_l > 2l+1$, estimating the missing orthogonal matrix $O_l$ is equivalent to estimating $A_l$. Since $S_l$ is a decreasing function of l, for some large enough l we would have $S_l < 2l+1$, that is, it has $O(L)$ degrees of freedom. In such cases, it does not make sense to estimate $O_L$ which has $O(L^2)$ degrees of freedom. But we can still estimate $A_L$ closest to $B_L$ using equation (1).

Figures 3B, 3C:
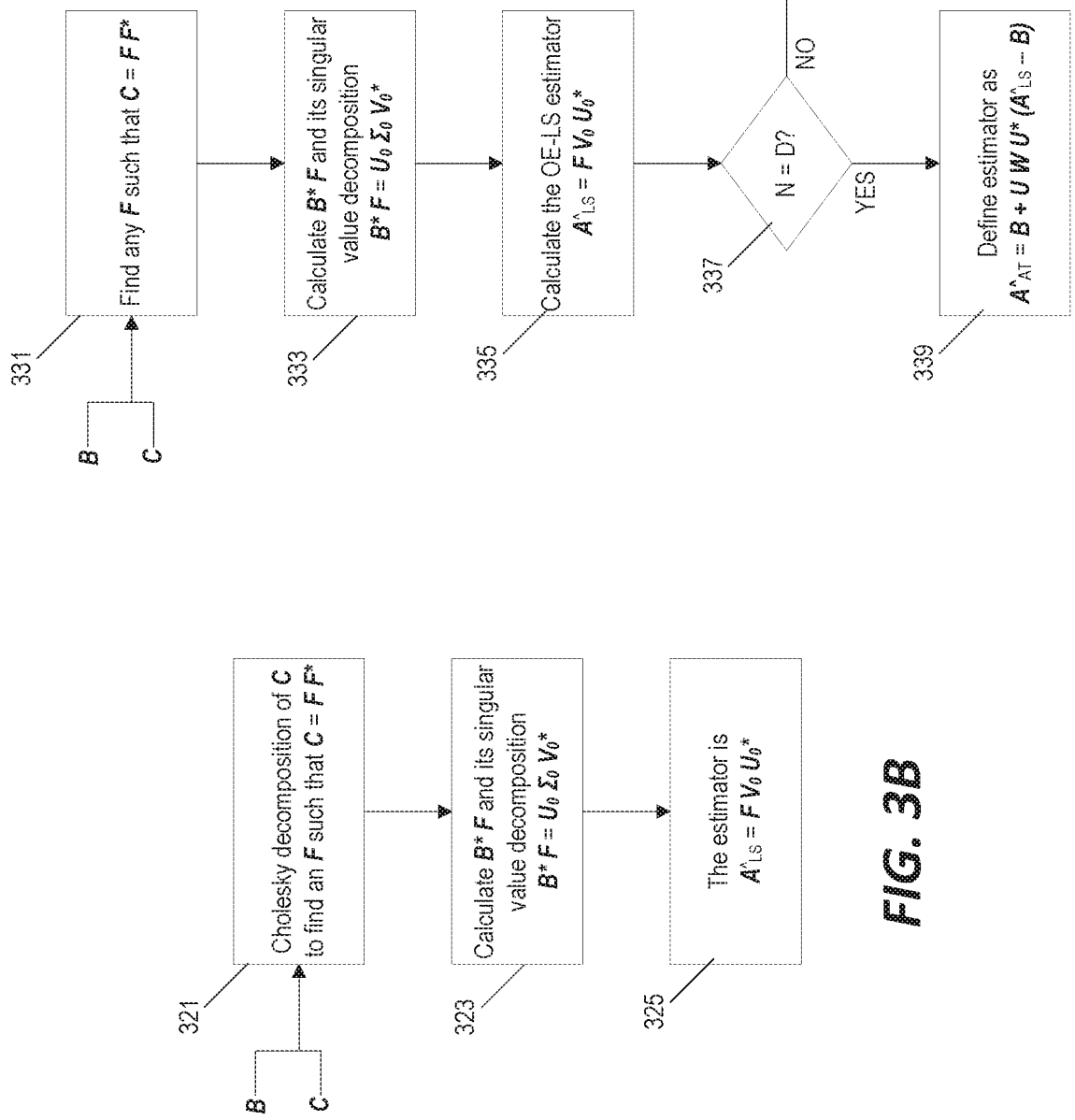
FIG. 3B is a flowchart of a method for estimating the missing orthogonal matrices in the method of FIG. 3A using orthogonal extension by least squares.
FIG. 3C is a flowchart of a method for estimating the missing orthogonal matrices in the method of FIG. 3A using orthogonal extension by anisotropic twicing.

In order to determine the 3D Fourier transform $F(\Phi_A)$ and thereby the 3D density $\Phi_A$, we need to determine the coefficient matrices $A_l$ of the spherical harmonic expansion. FIG. 3B illustrates an example using OE in which the coefficient matrices $A_l$ are estimated with the aid of a homologous structure $\Phi_B$ using a least squares estimator. Suppose $\Phi_B$ is a known homologous structure whose 3D Fourier transform $F(\Phi_B)$ has the following spherical harmonic expansion:

$$F(\Phi_B)(k,\theta,\varphi) = \Sigma_{l=0}^{\infty} \Sigma_{m=-l}^{l} B_{lm}(k) Y_l^m(\theta,\varphi) \tag{10}$$

In practice, the homologous structure $\Phi_B$ is available at some finite resolution, therefore only a finite number of coefficient matrices $B_l$ (l=0, 1, ..., $L_B$) are given. We show how to estimate the unknown structure $\Phi_A$ up to the resolution dictated by the input images and the resolution of the homologous structure through estimating the coefficient matrices $A_l$ for l=0, 1, ..., $L_A$ where $L_A = \min(L, L_B)$.

Let $F_l$ be any matrix of size $S_l \times 2l+1$ satisfying $C_l = F_l F_l^*$, determined from the Cholesky decomposition of $C_l$ (step 321). Then, using equation (9)

$$A_l = F_l O_l \tag{11}$$

where $O_l \in O(2l+1)$ for $S_l > 2l+1$. Using the assumption that the structures are homologous, $A_l \approx B_l$, one can determine $O_l$ as the solution to the least squares problem $$O_l = \underset{O \in O}{\arg} \min_{(2l+1)} \|F_l O - B_l\|_F^2 \tag{12}$$

where $\|\cdot\|_F$ denotes the Frobenius norm. Although the orthogonal group is non-convex, there is a closed form solution to equation (12) given by $$O_l = V_l U_l^T \tag{13}$$

where $$B_l^* F_l = U_l \Sigma_l V_l^T \tag{14}$$

is a singular value decomposition (SVD) of $B_l^* F_l$ (step 323). Thus, $A_l$ can be estimated by the following least squares estimator (step 325):

$$\hat{A}_{l,LS} = F_l V_l U_l^T \tag{15}$$

Hereafter, we drop the subscript l for convenience, since the procedure can be applied to each l separately.

As a natural generalization, one may wonder whether the estimator $2\hat{A}_{LS} - B$ (i.e., an estimator utilizing twicing) is unbiased for (N,D)≠(1,1). We assume that A is sampled from the model A=FV, wherein F F*=C and V is a random orthogonal matrix (or a random unitary matrix) sampled from the uniform distribution with Haar measure over the orthogonal group when A is a real-valued matrix or the unitary group (when A is a complex-valued matrix). This probabilistic model is reasonable for equation (1), because when A A* is given, F is known and V is an unknown orthogonal or unitary matrix, that is, we have no prior information about V. In addition, we assume the B is a matrix close to A such that A−B is fixed. An unbiased estimator of A which is an affine transformation of $\hat{A}_{LS}$ is determined as follows.

When N=D, assuming that the spectral decomposition of C is given by $C = U \text{diag}(\lambda_1, \lambda_2, \ldots, \lambda_D) U^*$, then using our probabilistic model we have $$\mathbb{E}[A - \hat{A}_{LS}] = UTU^*(A-B) + o(\|A-B\|_F) \tag{16}$$

where T is a diagonal matrix with $i^{th}$ diagonal entry given by $$T_{ii} \begin{cases} \dfrac{1}{D}\left[-\dfrac{1}{2} + \sum_{1 \leq j \leq D} \dfrac{\lambda_i^2}{\lambda_i^2 + \lambda_j^2}\right] & \text{when } A, C \in \mathbb{R}^{D \times D} \\ \dfrac{1}{D} \sum_{1 \leq j \leq D} \dfrac{\lambda_i^2}{\lambda_i^2 + \lambda_j^2} & \text{when } A, C \in \mathbb{C}^{D \times D} \end{cases}$$

and $f(X) = o(\|X\|_F)$ means that $\lim \sup_{\|X\|_F \to 0} f(X)/\|X\|_F \to 0$.

From equation (16), we have $(-I+UTU^*)(A-B) = B - \mathbb{E}[\hat{A}_{LS}] + o(\|A-B\|_F)$ and an asymptotically consistent estimator of A is given by $$\hat{A}_{AT} = B - (I - UTU^*)^{-1}(B - \hat{A}_{LS}) = B + UWU^*(\hat{A}_{LS} - B) \tag{17}$$

where $W = (I-T)^{-1}$. When $A, B \in \mathbb{C}^{1 \times 1}$, the matrices reduce to scalars: U=1, T=½, W=2, and $\hat{A}_{AT} = B + 2(\hat{A}_{LS} - B)$.

From equation (16), it follows that $$[A] = \mathbb{E}[\hat{A}_{LS}] + UTU^*(A-B) + o(\|A-B\|_F) \tag{18}$$

A could be approximated in the right-hand-side of equation (18) by $\hat{A}_{LS}$, which leads to a new estimator $\hat{A}_T^{(1)} = \hat{A}_{LS} + UTU^*(\hat{A}_{LS} - B)$. In fact, there exists a family of estimators by approximating A recursively in the right-hand-side of equation (18) by $\hat{A}_T^{(t-1)}$ with $\hat{A}_T^{(0)} = \hat{A}_{LS}$:

$$\hat{A}_T^{(t)} = \hat{A}_{LS} + UTU^*(\hat{A}_T^{(t-1)} - B) \tag{19}$$

This family of estimators can be written explicitly as $$\hat{A}_T^{(t)} = B + U(I + T + T^2 + \ldots + T^t)U^*(\hat{A}_{LS} - B) \tag{20}$$

Using $W = (I-T)^{-1} = \Sigma_{i=0}^{\infty} T^i$, we have that $\hat{A}_T^{(t)} = \hat{A}_{AT}$ as $t \to \infty$. In general, this family of estimators has smaller variance than $\hat{A}_{AT}$, but larger bias since they are not unbiased (see, e.g., FIGS. 4A and 4B).

If N>D, then the column space A is the same as the column space of C. Let P be the projector of size N×D to this column space, then we have A=PP*A. As a result, to find an unbiased estimator of A, it is sufficient to find an unbiased estimator of P*A, which is a square matrix. Since P/A is close to P*B and (P*A)(P*A)*=P*CP* is known, an unbiased estimator of P*A can be obtained through equation (17), with B replaced by PB and C replaced by P*CP*. In summary, an unbiased estimator of A can be obtained in two steps: First, find $\hat{A}_{AT}^{(O)}$, an unbiased estimator of P*A, by applying equation (17), with B replaced by P*B and C replaced by P*C P*. Second, an unbiased estimator of A is obtained by $\hat{A}_{AT}=P \hat{A}_{AT}^{(O)}$.

If N<D, we use the following heuristic estimator. Let P be a matrix of size D×N that is the projector to the row space of B, and assuming that Â, the estimator of A, has the same row space as B, then $\hat{A}=\hat{A}PP*$, and it is sufficient to find AP, and estimator of AP. With (AP)(AP)*=AA*=C known and the fact that AP is close to BP, we may use estimator of equation (17). In summary, we use the following procedure: First, find $\hat{A}_{AT}^{(O)}$, an estimator of AP, by applying the estimator of equation (17), with B replaced by BP and, second, an estimator of A is obtained by $\hat{A}_{AT}=\hat{A}_{AT}^{(O)}P*$.

We remark that for N<D, there is no theoretical guarantee to show that it is an unbiased estimator, unlike the setting N≥D. However, the assumption that Â has the same column space as B is reasonable and the proposed estimator performs well in practice.

The autocorrelation matrices $C_l$ are derived from the covariance matrix Σ of the 2D Fourier transformed projection images through the equation:

$$C_l(|k_1|,|k_2|)=2\pi(2l+1)\int_0^\pi \Sigma(|k_1|,|k_2|,\psi)P_l(\cos \psi)\sin \psi d\psi \quad (21)$$

where ψ is the angle between the vectors $k_1$ and $k_2$ in the x-y plane. We estimate the covariance matrix Σ of the underlying 2D Fourier transformed clean projection images. This estimation method provides a more accurate covariance compared to a classical sample covariance matrix. First, it corrects for the CTF. Second, it performs eigenvalue shrinkage, which is critical for high dimensional statistical estimation problems. Third, it exploits the block diagonal structure of the covariance matrix in a steerable basis, a property that follows from the fact that any experimental image is just as likely to appear in different in-place rotations. A steerable basis consists of outer products of radial functions (such as Bessel functions) and Fourier angular modes. Each block along the diagonal corresponds to a different angular frequency. Moreover, the special block diagonal structure facilitates fast computation of the covariance matrix.

Since the autocorrelation matrix $C_l$ estimated from projection images can have a rank exceeding 2l+1, we first find its best rank 2l+1 approximation via singular value decomposition, before computing its Cholesky decomposition. In the case of symmetric molecules, we use the appropriate rank as dictated by classical representation theory of SO(3) (less than 2l+1).

FIG. 3C illustrates a method for estimating the 3D structure of a target molecule using anisotropic twicing as described above (particularly in reference to equations (16) through (21)). Given a known structure B of a homologous molecule and a covariance matrix C of the target molecule, the system is configured to find a matrix $F \in \mathbb{C}^{N \times D}$ such that C=F F* (step 331). Next, the system calculates BF and its singular value decomposition $B*F=U_0\Sigma_0V_0*$ (step 333). The system then calculates the OE-LS estimator as described in FIG. 3B (step 335). If N=D (step 337), then the anisotropic twicing estimator is defined as $\hat{A}_{AT}=B+UWU*(\hat{A}_{LS}-B)$ (step 339). If N>D (step 341), then the anisotropic twicing estimator is defined as $\hat{A}_{AT}=P\hat{A}_{AT}^{(O)}$ assuming that P is a projectors of size N×D to the D-dimensional subspace spanned by the columns of C (step 343). If N<D, Then the anisotropic twicing estimator is defined as $\hat{A}_{AT}=\hat{A}_{AT}^{(O)} P*$ where P is a projector of size D×N to the N-dimensional subspace in $\mathbb{R}^D$ spanned by the rows of B (step 345).

For any parameter θ, the performance of its estimator θ^ can be measured in terms of its mean squared error (MSE), $\mathbb{E}\|\theta-\theta\hat{}\|^2$. The MSE of any estimator can be decomposed into its bias and variance:

$$\text{MSE}=[\|\theta-\theta\hat{}\|^2]=\|\text{bias}\|^2+\text{var} \quad (22)$$

where $$\text{Bias}=[\theta\hat{}]-\theta \quad (23)$$

and $$\text{Var}=[\|\theta\hat{}-\mathbb{E}[\theta\hat{}]\|^2] \quad (24)$$

Figure 4B:
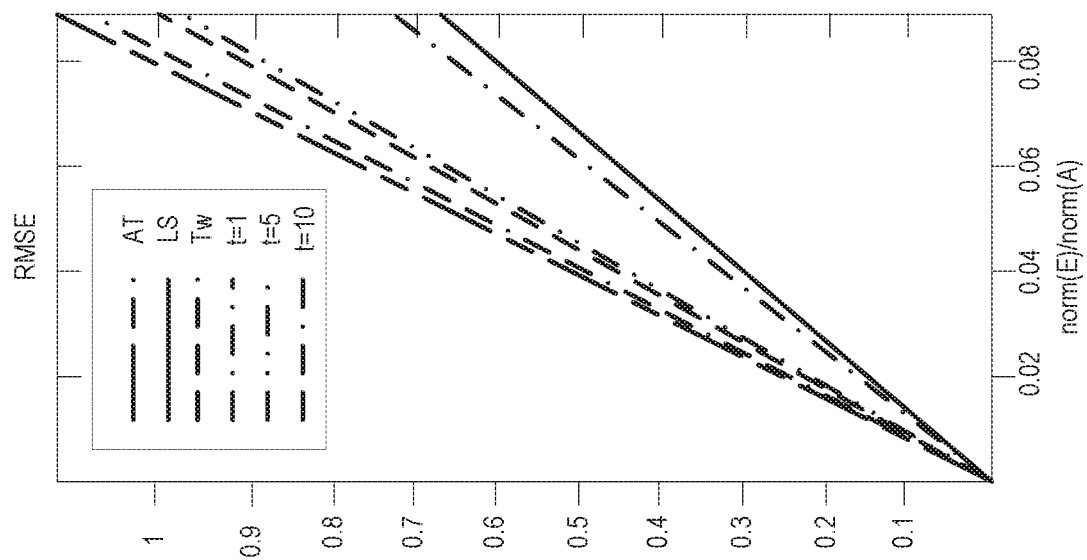
FIG. 4B is a graph of the RMSE of the anisotropic twicing, least squares, and twicing estimators and also the family of estimators with t=1, 5, 10 averaged over 1000 experiments.
Figure 4A:
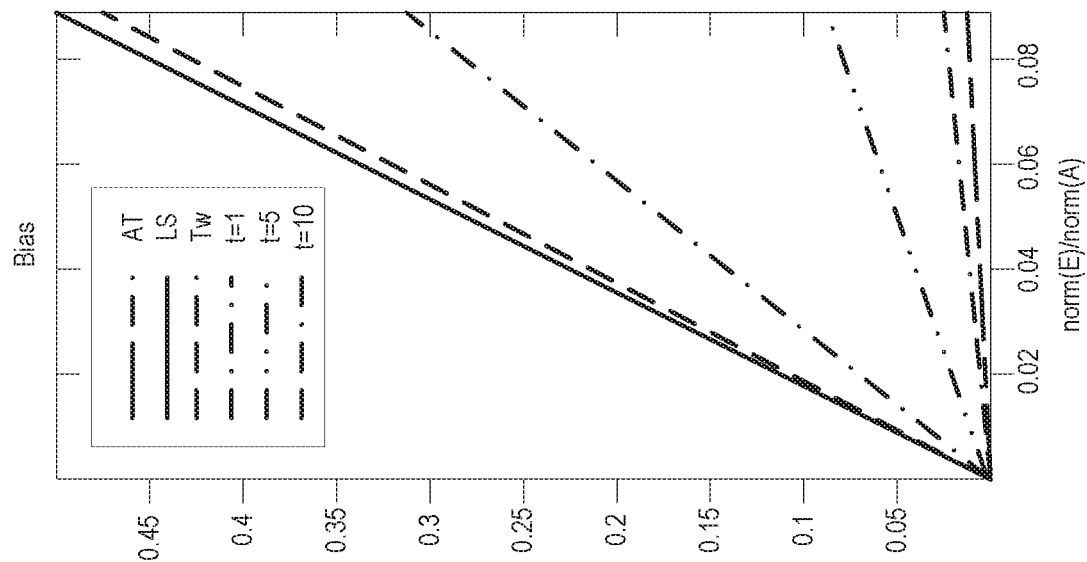
FIG. 4A is a graph of the bias of the anisotropic twicing, least squares, and twicing estimators and also the family of estimators with t=1, 5, 10 averaged over 1000 experiments.

Unbiased estimators are often not optimal in terms of MSE, but they can be valuable for being unbiased. In the examples below describe a numerical experiment starting with a fixed $F \in \mathbb{R}^{10 \times 10}$ and an unknown matrix A=FO where O is a random orthogonal $\mathbb{R}$ matrix. We are given a known similar matrix B such that A=B+E. The goal is to estimate A given B and F. FIG. 4A shows a comparison of the bias and FIG. 4B shows a comparison of the root mean squared error (RMSE) of different estimators averaged over 10,000 runs of the numerical experiment: the anisotropic twicing estimator, the twicing estimator, the least squares estimator, and estimators from the family of estimators for some values of t. The figures demonstrate that the anisotropic twicing estimator is asymptotically unbiased at the cost of higher MSE.

Figure 5A:
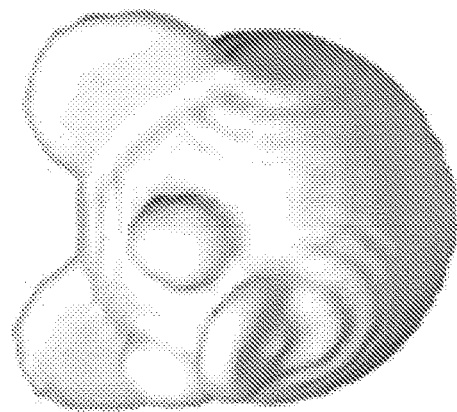
FIG. 5A is an example of a 3D structure of a target molecule.

FIGS. 5A, 5B, 5C, and 5D illustrate another numeric example using synthetic datasets generated from an artificial molecule. FIG. 5A illustrates the target molecule made up of ellipsoids with the density set to 1 inside the ellipsoids and set to zero outside. The target molecule illustrated in FIG. 5A includes a small ellipsoid 501 that is not present in the homologous molecule. This represents the small perturbation E. When the Fourier volume B+E is expanded in the truncated spherical Bessel basis described above, the average relative perturbation $\|E_l\|/\|A_l\|$ for the first few coefficients in the truncated spherical harmonic expansion for l=1, . . . 10 is 8%.

Figure 5B:
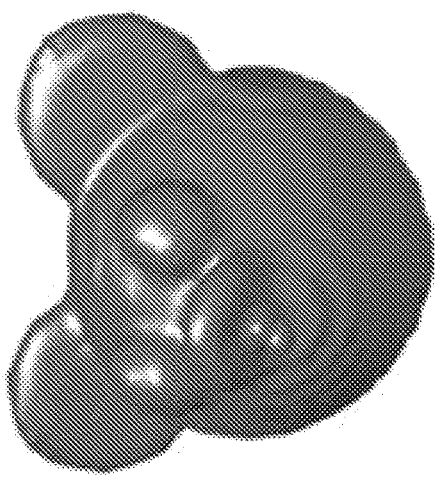
FIG. 5B is an example of the 3D structure of the target molecule of FIG. 5A reconstructed using a least squares estimator.
Figure 5C:
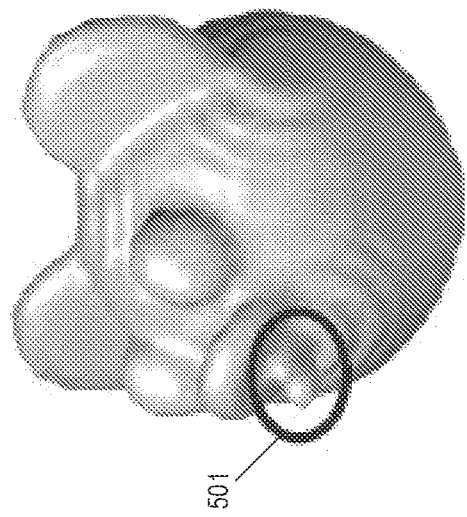
FIG. 5C is an example of the 3D structure of the target molecule of FIG. 5A reconstructed using a twicing estimator.
Figure 5D:
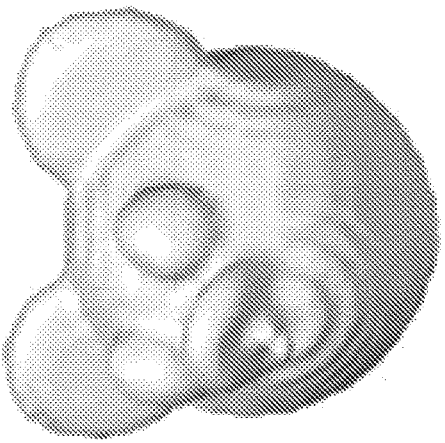
FIG. 5D is an example of the 3D structure of the target molecule of FIG. 5A reconstructed using an anisotropic twicing estimator.

Next we generated 10,000 projection images from the volume of the artificial molecule of FIG. 5A. We then employed OE to reconstruct the volume A (as illustrated in FIG. 5A) from a known homologous structure B (similar to the volume in FIG. 5A, but without the additional ellipsoid 501). FIG. 5B shows the reconstructed volume using a least squares estimator. FIG. 5C shows the reconstructed volume using a twicing estimator. FIG. 5D shows the reconstructed volume using an anisotropic twicing estimator. We note that, while all three estimators are able to recover the additional subunit 501, the anisotropic twicing estimator of FIG. 5D best recovers the unknown subunit to its correct relative magnitude. The relative error in the region of the unknown subunit 501 is 59% with least squares, 31% with twicing, and 19% with anisotropic twicing.

Figure 6A:
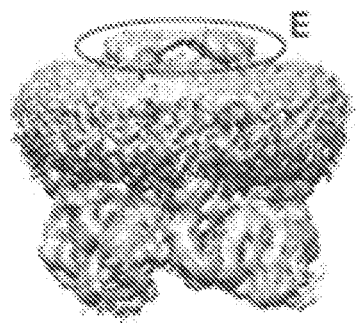
FIG. 6A is an elevation view of an example of a target molecule.
Figure 6B:
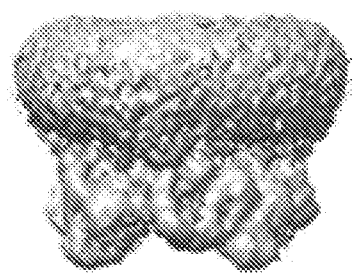
FIG. 6B is an elevation view of an example of a homologous molecule similar in structure to the target molecule of FIG. 6A.
Figure 6C:
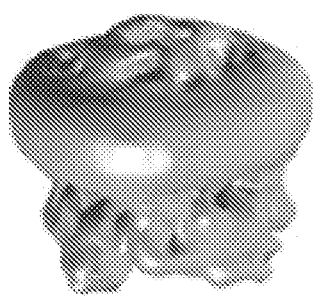
FIG. 6C is a reconstruction of the target molecule of FIG. 6A.
Figure 6D:
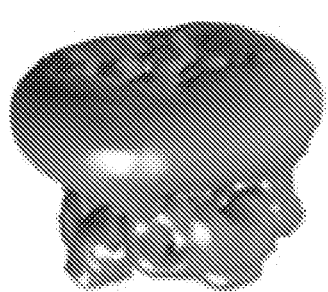
FIG. 6D is a reconstruction of the homologous molecule of FIG. 6B.
Figure 6E:
FIG. 6E is an example of the 3D structure of the target molecule of FIG. 6A reconstructed using a least squares estimator.
Figure 6F:
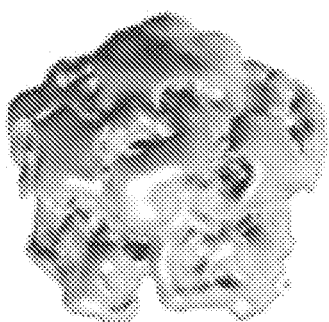
FIG. 6F is an example of the 3D structure of the target molecule of FIG. 6A reconstructed using a twicing estimator.
Figure 6G:
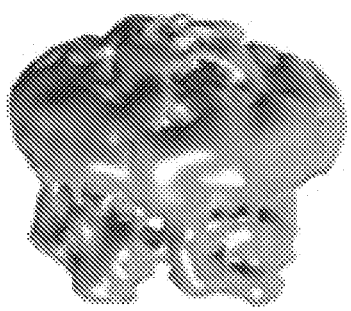
FIG. 6G is an example of the 3D structure of the target molecule of FIG. 6A reconstructed using an anisotropic twicing estimator.

FIGS. 6A through 6G illustrate another example using a synthetic dataset generated from a TRPV1 molecule (with imposed $C_4$ rotational symmetry) in complex with DkTx and RTX (A). This volume is available on EMDB as EMDB-8117. The actual 3D structure of the target molecule is illustrated in FIG. 6A and the homologous molecule (i.e., the "known" structure) is illustrated in FIG. 6B. The small additional subunit E is visible in FIG. 6A as an extension over the top of the molecule. This represents the small perturbation E (i.e., the difference between the target molecule structure A and the known homologous molecule structure B). FIG. 6C illustrates the "ground truth" representation of the structure of the target molecule A while FIG. 6D illustrates the formulaic representation of the homologous structure B. A total of 26,000 projection images were generated from A (i.e., the volume as illustrated in FIG. 6C), the effects of both CTF and additive white Gaussian noise were added, and then OE techniques were used to reconstruct the volume A. FIG. 6E shows the reconstruction of the target molecule structure using a least squares estimator, FIG. 6F shows the reconstruction using a twicing estimator, and FIG. 6O shows the reconstruction using an anisotropic twicing estimator. The $C_4$ symmetry was taken into account in the autocorrelation analysis by including in equation (2) only symmetry-invariant spherical harmonics $Y_l^m$ for which m=0 mod 4.

Again, all three estimators are able to recover the additional subunit E, but the anisotropic twicing estimator best recovers the unknown subunit to its correct relative magnitude. The relative error in the unknown subunit is 43% with least squares, 56% with twicing, and 30% with anisotropic twicing.

In the example of FIGS. 6A through 6G, OE techniques were applied to experimental data of the TRPV1 molecule in complex with DkTx and RTX, determined in lipid nanodisc, available on the public database Electron Microscopy Pilot Image Archive (EMPIAR) as EMPIAR-10059, and the 3D reconstruction is available on the electron microscopy data bank (EMDB) as EMDB-8117. The dataset consists of 73,000 motion corrected, picked particle images (which were used for the reconstruction in EMDB-8117 (FIG. 6A)) of size 192×192 with a pixel size of 1.3 A. The 3D structure of TRPV1 alone was used as the "homologous structure." This is available on EMBD as EMDB-8118. The two structures differ only by a small DkTx and RTX subunit at the top, which can be seen in FIG. 6A.

Since the noise in the experimental images is colored while our covariance estimation procedure requires white noise, we first preprocess the raw images in order to "whiten" the noise. We estimate the power spectrum of noise using the corner pixels of all images. The images are then whitened using the estimated noise power spectrum. In the context of our mathematical model, the volume EMDB-8117 of TRPV1 with DkTx and RTX is the unknown volume A and the volume EMDB-8118 of TRPV1 alone is the known, similar volume B. We use OE to estimate A given B and the raw, noisy projection images of A from the experimental dataset.

Figure 7A:
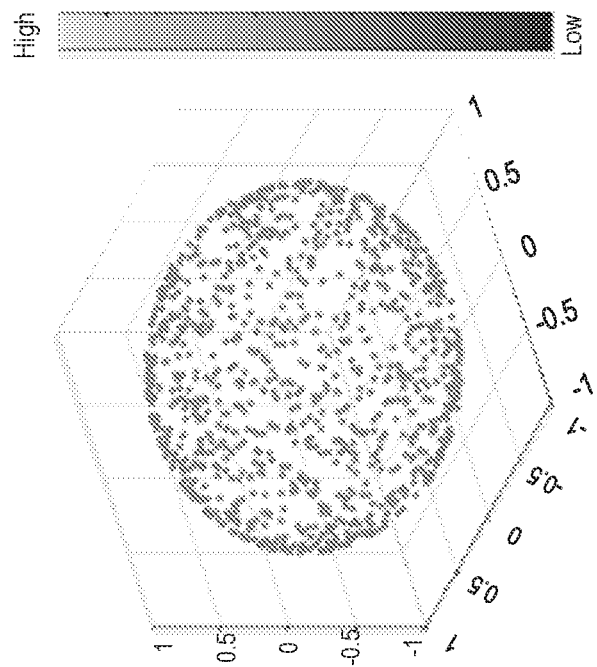
FIG. 7A is a graph of the non-uniform viewing angle distribution of the images used to reconstruct the 3D structures.
Figure 7B:
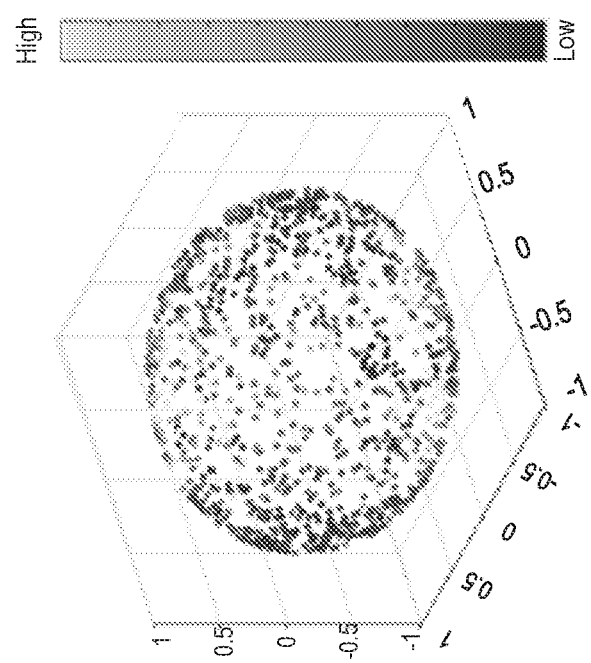
FIG. 7B is a graph of the uniform viewing angle distribution after sampling of the images used to reconstruct the 3D structures.

The basis assumption in Kam's theory is that the distribution of viewing angles is uniform. This assumption is difficult to satisfy in practice, since molecules in the sample can often have preference for certain orientations due to their shape and mass distribution. The viewing angle distribution in EMPIAR-10059 is non-uniform as illustrated in FIG. 7A. As a robustness test, we attempt 3D reconstruction with (i) all images, such that the viewing angle distribution is non-uniform (i.e., FIG. 7A) and (ii) by sampling images such that the viewing angle distribution of the images is approximately uniform (as shown in FIG. 7B). For the sampling procedure, we chose 10,000 points at random from the uniform distribution on the sphere and classify each image into these 10,000 bins based on the point closest to it. We discard bins that have no images, and for the remaining bins we pick a maximum of 3 points per bin. We use the selected images (slightly less than 30,000) for reconstruction with roughly uniformly distributed viewing angles.

Figure 8C:
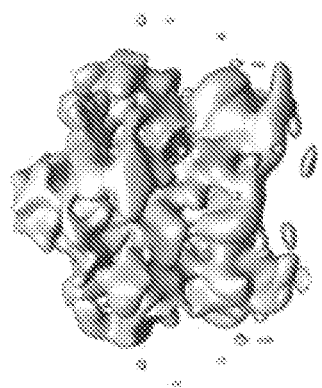
FIG. 8C is an example of a 3D structure of the target molecule of FIG. 6A reconstructed using an anisotropic twicing estimator and approximately 30,000 two-dimensional images of the target molecule with an approximately uniform viewing angle distribution.
Figure 9C:
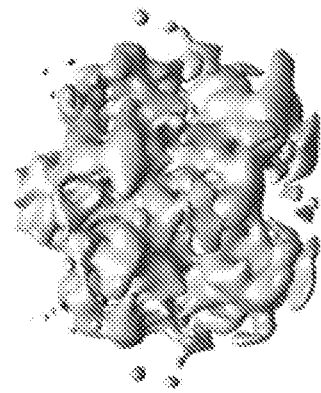
FIG. 9C is an example of a 3D structure of the target molecule of FIG. 6A reconstructed using an anisotropic twicing estimator and approximately 73,000 two-dimensional images of the target molecule with a non-uniform viewing angle distribution.
Figure 8B:
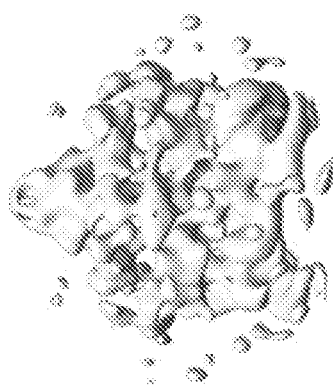
FIG. 8B is an example of a 3D structure of the target molecule of FIG. 6A reconstructed using a twicing estimator and approximately 30,000 two-dimensional images of the target molecule with an approximately uniform viewing angle distribution.
Figure 9B:
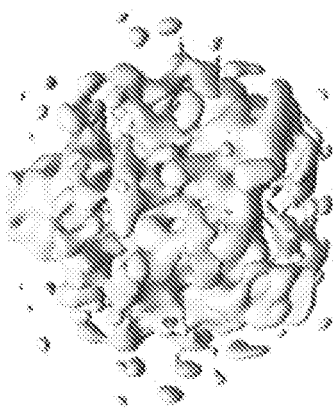
FIG. 9B is an example of a 3D structure of the target molecule of FIG. 6A reconstructed using a twicing estimator and approximately 73,000 two-dimensional images of the target molecule with a non-uniform viewing angle distribution.
Figure 8A:
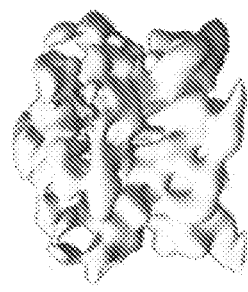
FIG. 8A is an example of the 3D structure of the target molecule of FIG. 6A reconstructed using a least square estimator and approximately 30,000 two-dimensional images of the target molecule with an approximately uniform viewing angle distribution.
Figure 9A:
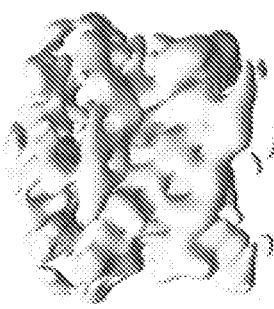
FIG. 9A is an example of the 3D structure of the target molecule of FIG. 6A reconstructed using a least square estimator and approximately 73,000 two-dimensional images of the target molecule with a non-uniform viewing angle distribution.
Figure 10A:
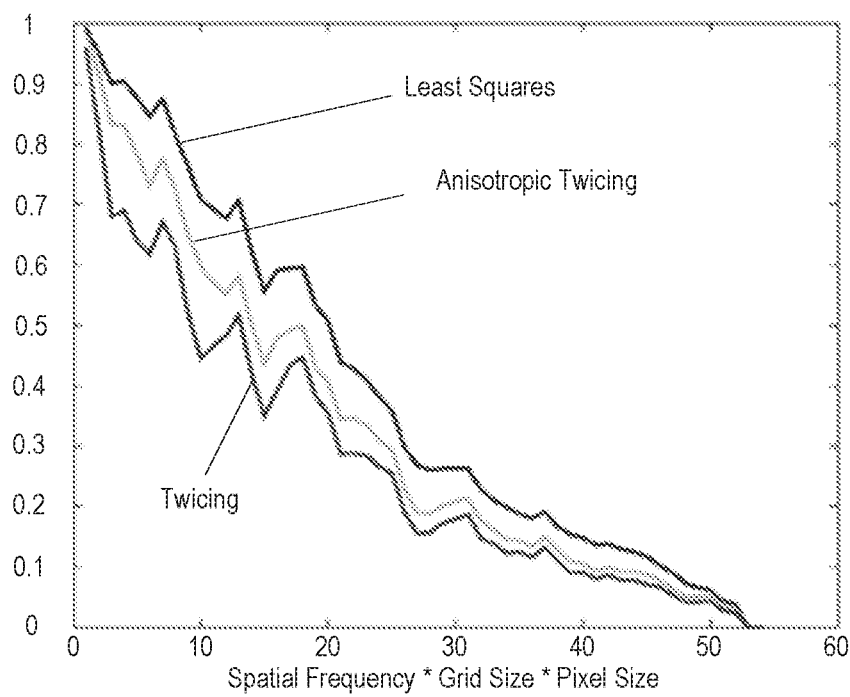
FIG. 10A is a graph of the FCR curve for the reconstruction of the entire molecule corresponding to the examples of FIGS. 8A, 8B, and 8C.
Figure 10B:
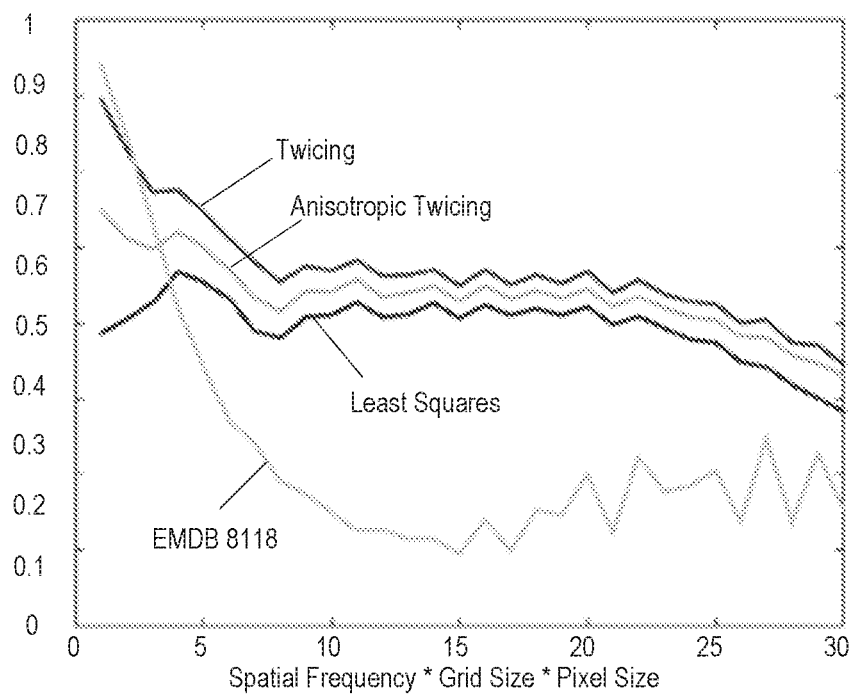
FIG. 10B is a graph of the FCR curve for the reconstruction of an unknown additional structural component of the molecule corresponding to the examples of FIGS. 8A, 8B, and 8C.

FIGS. 8A, 8B, and 8C illustrate the 3D reconstructions of the TRPV1 in complex with DkTx and RTX (EMPIAR-10059) using least squares, twicing, and anisotropic twicing, respectively, based on the images selected by sampling to impose approximately uniform viewing angle distribution. FIGS. 9A, 9B, and 9C illustrate the 3D reconstructions of the TRPV1 in complex with DkTx and RTX (EMPIAR-10059) using least squares, twicing, and anisotropic twicing, respectively, based on all 73,000 images such that the viewing angle distribution is non-uniform. FIG. 10A shows the FCR curve for the reconstruction of the entire molecule obtained by OE using the least squares, twicing, and anisotropic twicing estimators corresponding to FIGS. 8A, 8B, and 8C. FIG. 10B shows the FCR curve for only the unknown subunit.

The methods described in the examples above were implemented in the UNIX environment on a computer with 60 cores running at 2.3 GHz with total RAM of 1.5 TB. Using 20 cores, the total time taken for preprocessing the 2D images (whitening, background normalization, etc.) and computing the covariance matrix was 1400 seconds. Calculating the autocorrelation matrices using equation (21) involved some numerical integration which took 790 seconds, but for a fixed c and R (statisfied for datasets of roughly similar size and quality) these can be precomputed. Computing the basis functions and calculating the coefficient matrices of the homologous structure took 30 seconds and recovering the 3D structure by applying the appropriate estimator (AT, twicing, or LS) and computing the volume from the estimated coefficients took 10 seconds.

The orthogonal retrieval problem in SPR is akin to the phase retrieval problem in x-ray crystallography. In crystallography, the measured diffraction patterns contain information about the modulus of the 3D Fourier transform of the structure but the phase information is missing and needs to be obtained by other means. In crystallography, the particle's orientations are known but the phase of the Fourier coefficients is missing, while in cryo-EM, the projection images contain phase information but the orientations of the particles are missing. Kam's autocorrelation analysis for SPR leads to an orthogonal retrieval problem which is analogous to the phase retrieval problem in crystallography. The phase retrieval problem is perhaps more challenging than the orthogonal matrix retrieval problem in cryo-EM. In crystallography, each Fourier coefficient is missing its phase, while in cryo-EM only a single orthogonal matrix is missing per several radial components. For each l, the unknown coefficient matrix $A_l$ is of size $S_l \times (2l+1)$, corresponding to $(2l+1)$ radial functions. Each $A_l$ is to be obtained from $C_l$, which is a positive semidefinite matrix of size $S_l \times S_l$ and rank at most 2l+1. For $S_l > 2l+1$, instead of estimating $S_l$ (2l+1) coefficients, we only need to estimate an orthogonal matrix in O(2l+1) which allows l(2l+1) degrees of freedom. Therefore, there are $(S_l-l)(2l+1)$ fewer parameters to be estimated.

In some implementations, OE requires a sufficient number of 2D images to estimate the covariance matrix to the desired level of accuracy, so it has a greater chance of success for homology modeling from noisy images than other ab-initio methods such as those based on commons line, which fail at high noise levels.

In the examples described above, various implementations provide, among other things, a general magnitude correction scheme for a class of phase-retrieval problems, in particular, for orthogonal extension in cryo-EM. In some implementations, the magnitude correction scheme includes a variation of "twicing" referred to herein as anisotropic twicing. An asymptotically unbiased estimator is describes and the examples demonstrate 3D homology modeling using OE with synthetic and experimental datasets. These and similar techniques can be used to provide models and to initialize refinement directly from experimental images without performing class averaging and orientation estimation in cryo-EM and XFEL.

While anisotropic twicing outperforms least squares and twicing for synthetic data, in the examples described above, the three estimation methods have similar performance for experimental data. One possible explanation is that the underlying assumption made by all estimation methods that $C_l$ are noiseless as implied by imposing the constraint $C_l = A_l A_l^*$ is violated more severely for certain types of experimental data. Specifically, the $C_l$ matrices are derived from the 2D covariance matrix of the images and estimation errors are the result of noise in the images, the finite number of images available, non-uniformity of viewing directions, and imperfect estimation of individual image noise power spectrum, contrast transfer function, and centering. These effects are likely to be more pronounced in some types of experimental data compared to synthetic data. As a result, the error in estimating the $C_l$ matrices from experimental data is larger. The error in the estimated $C_l$ can be taken into consideration by replacing the constrained least squares problem of equation (1) with the regularized least squares problem $$\min_A \|A-B\|_F^2 + \lambda \|C-AA^*\|_F^2 \quad (25)$$

where $\lambda > 0$ is a regularization parameter that would depend on the spherical harmonic order l.

Thus, the invention provides, among other things, methods and systems for generating a reconstruction of a 3D structure of an object (such as, for example, a target molecule) based on a low order moment of 2D image data for the object and prior knowledge of a similar, homologous 3D structure. Various features and advantages of the invention are set forth in the following claims.

What is claimed is:

1. A method for digitally reconstructing an unknown 3D structure of a target molecule, the method comprising:
   receiving, by an electronic processor, a plurality of 2D images of the target molecule captured by an imaging system;
   calculating, by the electronic processor, an estimated low order moment of the unknown 3D structure of the target molecule based on the plurality of 2D images;
   identifying a homologous molecule having a known 3D structure;
   determining, by the electronic processor, at least one expansion coefficient of the known 3D structure of the homologous molecule;
   calculating, by the electronic processor, at least one estimated expansion coefficient for the unknown 3D structure based at least in part on the estimated low order moment of the unknown 3D structure of the target molecule and the at least one expansion coefficient of the known 3D structure of the homologous molecule; and
   generating, by the electronic processor, an estimated 3D reconstruction of the target molecule based on the at least one estimated expansion coefficient for the unknown 3D structure of the target molecule.

2. The method of claim 1, further comprising outputting on a display screen a visual representation of the estimated 3D reconstruction of the target molecule.

3. The method of claim 1, further comprising storing the estimated 3D reconstruction of the target molecule to a non-transitory computer-readable memory.

4. The method of claim 1, wherein calculating the estimated low order moment of the unknown 3D structure of the target molecule based on the plurality of 2D images includes calculating a covariance matrix from the plurality of 2D images.

5. The method of claim 4, further comprising calculating at least one autocorrelation matrix based on the covariance matrix, and
   wherein calculating the at least one estimated expansion coefficient for the unknown 3D structure based at least in part on the estimated low order moment of the unknown 3D structure of the target molecule and the at least one expansion coefficient of the known 3D structure of the homologous molecule includes calculating a set of expansion coefficients for the unknown 3D structure based at least in part on the at least one autocorrelation matrix.

6. The method of claim 4, further comprising capturing a plurality of noisy two-dimensional projection images of the target molecule using a cryo-electron microscopy system, and wherein calculating the covariance matrix includes calculating an estimated covariance matrix indicative of a plurality of clean two-dimensional projection images of the target molecule based on the plurality of noisy two-dimensional projection images.

7. The method of claim 1, further comprising expanding 2D image data from the plurality of 2D images in a truncated steerable basis, and wherein calculating the estimated low order moment includes calculating an estimated covariance matrix by applying a steerable principal component analysis to the expanded 2D image data.

8. The method of claim 1, wherein identifying a homologous molecule having the known 3D structure includes identifying the homologous molecule that is similar to the target molecule and is expected to have a similar 3D structure.

9. The method of claim 8, further comprising accessing a previous reconstruction of the known 3D structure of the homologous molecule from a non-transitory computer-readable memory.

10. The method of claim 1, further comprising
    calculating, by the electronic processor, a plurality of estimated spherical harmonic expansion coefficients for the unknown 3D structure, wherein the plurality of estimated spherical harmonic expansion coefficients for the unknown 3D structure does not include at least one missing orthogonal matrix that cannot be recovered from the plurality of 2D images of the target molecule because image data of the target molecule in the plurality of 2D images is incomplete, and
    wherein calculating the at least one estimated expansion coefficient of the unknown 3D structure includes
      estimating the at least one missing orthogonal matrix based at least in part on data indicative of the known 3D structure of the homologous molecule using orthogonal extension, and
      recovering a set of estimated spherical harmonic expansion coefficients for the unknown 3D structure of the target molecule based on the plurality of estimated spherical harmonic expansion coefficient for the unknown 3D structure and the estimated at least one missing orthogonal matrix.

11. The method of claim 10, wherein estimating the at least one missing orthogonal matrix using orthogonal extension includes applying an anisotropic estimator.

12. The method of claim 11, wherein applying the anisotropic estimator includes calculating the at least one missing orthogonal matrix $\hat{A}_{AT}$, where $\hat{A}_{AT} = B - UWU^*[B - \hat{A}_{LS}]$, where B is indicative of the known 3D structure of the homologous molecule, where $\hat{A}_{LS}$ is a least squares estimator of the at least one missing orthogonal matrix and is equal to $FV_0U_0^*$.

13. The method of claim 11, wherein applying the anisotropic estimator includes calculating the at least one missing orthogonal matrix $\hat{A}_{AT}$, where $\hat{A}_{AT} = P\hat{A}_{AT}^{(0)}$, and where P is a projector of size N×D to the D-dimensional subspace spanned by the columns of the autocorrelation matrix.

14. The method of claim 11, wherein applying the anisotropic estimator includes calculating the at least one missing orthogonal matrix $\hat{A}_{AT}$, where $\hat{A}_{AT} = \hat{A}_{AT}^{(0)} P^*$, and where $P^*$ is a projector of size D×N to the N-dimensional subspace in $\mathbb{R}^D$ spanned by the rows of a matrix B indicative of the known 3D structure of the homologous molecule.

15. The method of claim 11, wherein applying the anisotropic estimator includes finding a $F \in \mathbb{C}^{N \times D}$ such that $C = F F^*$, wherein $C \in \mathbb{C}^{N \times N}$, calculating $B^*F$ and calculating its singular value decomposition $B^*F = U_0 \Sigma_0 V_0^*$, where $B \in \mathbb{C}^{N \times D}$ and is indicative of the known 3D structure of the homologous molecule, calculating an orthogonal extension least-squares estimator of the at least one missing orthogonal matrix $\hat{A}_{LS}$, where $\hat{A}_{LS}$ is equal to $FV_0U_0^*$, and calculating the at least one missing orthogonal matrix $\hat{A}_{AT}$, wherein when N=D, $\hat{A}_{AT}$ is calculated as $B - UWU^*[B - \hat{A}_{LS}]$, when N>D, $\hat{A}_{AT}$ is calculated as $P\hat{A}_{AT}^{(0)}$, and P is a projector of size N×D to the D-dimensional subspace spanned by the columns of the autocorrelation matrix, and when N<D, $\hat{A}_{AT}$ is calculated as $\hat{A}_{AT}^{(0)} P^*$, and $P^*$ is a projector of size D×N to the N-dimensional subspace in $\mathbb{R}^D$ spanned by the rows of a matrix B indicative of the known 3D structure of the homologous molecule.

* * * * *